US012588847B2

(12) United States Patent
    Shinada

(10) Patent No.: US 12,588,847 B2
(45) Date of Patent: Mar. 31, 2026

(54) BIOMAGNETISM MEASURING DEVICE AND METHOD FOR CONTROLLING BIOMAGNETISM MEASURING DEVICE

(71) Applicant: SHIMADZU CORPORATION, Kyoto (JP)

(72) Inventor: Kei Shinada, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 0 days.

(21) Appl. No.: 18/723,353

(22) PCT Filed: Oct. 28, 2022

(86) PCT No.: PCT/JP2022/040420
    § 371 (c)(1),
    (2) Date: Jun. 21, 2024

(87) PCT Pub. No.: WO2023/119872
    PCT Pub. Date: Jun. 29, 2023

(65) Prior Publication Data
    US 2025/0057456 A1      Feb. 20, 2025

(30) Foreign Application Priority Data
    Dec. 22, 2021      (JP) ................................. 2021-208319

(51) Int. Cl.
    *A61B 5/242*        (2021.01)
    *A61B 5/00*         (2006.01)
                    (Continued)

(52) U.S. Cl.
    CPC ............ *A61B 5/242* (2021.01); *A61B 5/7271* (2013.01); *G01R 33/26* (2013.01); *A61B 5/243* (2021.01);
                    (Continued)

(58) Field of Classification Search
    CPC ....... A61B 5/242; A61B 5/7271; A61B 5/243; A61B 5/245; A61B 5/00; A61B 2560/0214; A61B 2562/0223; G01R 33/26
    See application file for complete search history.

(56) References Cited

U.S. PATENT DOCUMENTS

| | | | | | |
|---|---|---|---|---|---|
| 3,714,552 | A | * | 1/1973 | Hirschel ................ | G01R 33/26 |
| | | | | | 324/304 |
| 5,036,278 | A | * | 7/1991 | Slocum .................. | G01R 33/26 |
| | | | | | 324/304 |

(Continued)

OTHER PUBLICATIONS

Morales, S., et al. "Magnetocardiography measurements with 4He vector optically pumped magnetometers at room temperature." Physics in Medicine & Biology 62.18 (2017): 7267. (Year: 2017).*

(Continued)

*Primary Examiner* — Sean D Mattson
(74) *Attorney, Agent, or Firm* — Muir Patent Law, PLLC

(57) ABSTRACT

Provided are a biomagnetic measuring device and a control method for a biomagnetic measuring device that can measure biomagnetism more accurately. A biomagnetic measuring device according to the present invention includes: a first magnetic sensor and a second magnetic sensor that each include a cell having an internal space, and detect biomagnetism utilizing an optical pumping action by plasma generated in the cell; a plasma generator that supplies electric power for generating plasma in the internal space of each of the cells included in the first magnetic sensor and the second magnetic sensor; and a power supply controller that controls the plasma generator to generate plasma in the first magnetic sensor from a first start time to a first end time and generate plasma in the second magnetic sensor from a second start time after the first start time to a second end time after the first end time.

6 Claims, 5 Drawing Sheets

(51) Int. Cl.
   G01R 33/26      (2006.01)
   *A61B 5/243*      (2021.01)
   *A61B 5/245*      (2021.01)

(52) U.S. Cl.
   CPC ....... *A61B 5/245* (2021.01); *A61B 2560/0214*
         (2013.01); *A61B 2562/0223* (2013.01)

(56)           References Cited

U.S. PATENT DOCUMENTS

2012/0062221 A1*   3/2012   Le Prado  ...............   G01R 33/26
                                            324/244
2014/0368193 A1*   12/2014   Morales  .................   G01R 33/26
                                            324/304
2021/0293913 A1*   9/2021   Mifune  .................   G01R 33/26

OTHER PUBLICATIONS

Fourcault, William, et al. "Helium-4 magnetometers for room-temperature biomedical imaging: toward collective operation and photon-noise limited sensitivity." Optics Express 29.10 (2021): 14467-14475.

Jensen, Kasper, et al. "Magnetocardiography on an isolated animal heart with a room-temperature optically pumped magnetometer." Scientific reports 8.1 (2018): 16218.

* cited by examiner

SENSOR 1

SENSOR 2

DETECTION CIRCUIT 1

DETECTION CIRCUIT 2

ON / OFF

BIOMAGNETISM MEASURING DEVICE AND METHOD FOR CONTROLLING BIOMAGNETISM MEASURING DEVICE

TECHNICAL FIELD

The present invention relates to a biomagnetic measuring device and a control method for a biomagnetic measuring device.

BACKGROUND ART

A biomagnetic measuring device, which can detect weak magnetism emitted from a subject and, for example, visualize a distribution of a magnetic field, includes a plurality of sensors, and acquires the distribution of the magnetic field in the subject based on a signal output from each sensor.

CITATION LIST

Patent Literature

Patent Literature 1: U.S. Pat. No. 7,038,450

SUMMARY OF INVENTION

Technical Problem

However, the conventional biomagnetic measuring device and the conventional control method for the biomagnetic measuring device do not take sufficient account of the fact that sensors adversely affect each other in magnetic measurement.

An object of the present invention is to provide a biomagnetic measuring device and a control method for a biomagnetic measuring device that can measure biomagnetism more accurately.

Solution to Problem

A biomagnetic measuring device according to the present invention includes: a first magnetic sensor and a second magnetic sensor that each include a cell having an internal space, and detect biomagnetism utilizing an optical pumping action by plasma generated in the cell; a plasma generator that supplies electric power for generating plasma in the internal space of each of the cells included in the first magnetic sensor and the second magnetic sensor; and a power supply controller that controls the plasma generator to generate plasma in the first magnetic sensor from a first start time to a first end time and generate plasma in the second magnetic sensor from a second start time after the first start time to a second end time after the first end time.

Advantageous Effects of Invention

The biomagnetic measuring device according to the present invention includes power supply means that controls the plasma generator so that periods during which plasma is generated in the first magnetic sensor and in the second magnetic sensor are not the same. With such a configuration, the magnetic sensors do not adversely affect each other in magnetic measurement, making it possible to provide a biomagnetic measuring device that can measure biomagnetism more accurately.

DESCRIPTION OF EMBODIMENTS

Hereinafter, configurations of a biomagnetic measuring device and a control method for a biomagnetic measuring device according to an embodiment of the present invention will be described with reference to the drawings.

First Embodiment

Figure 1:
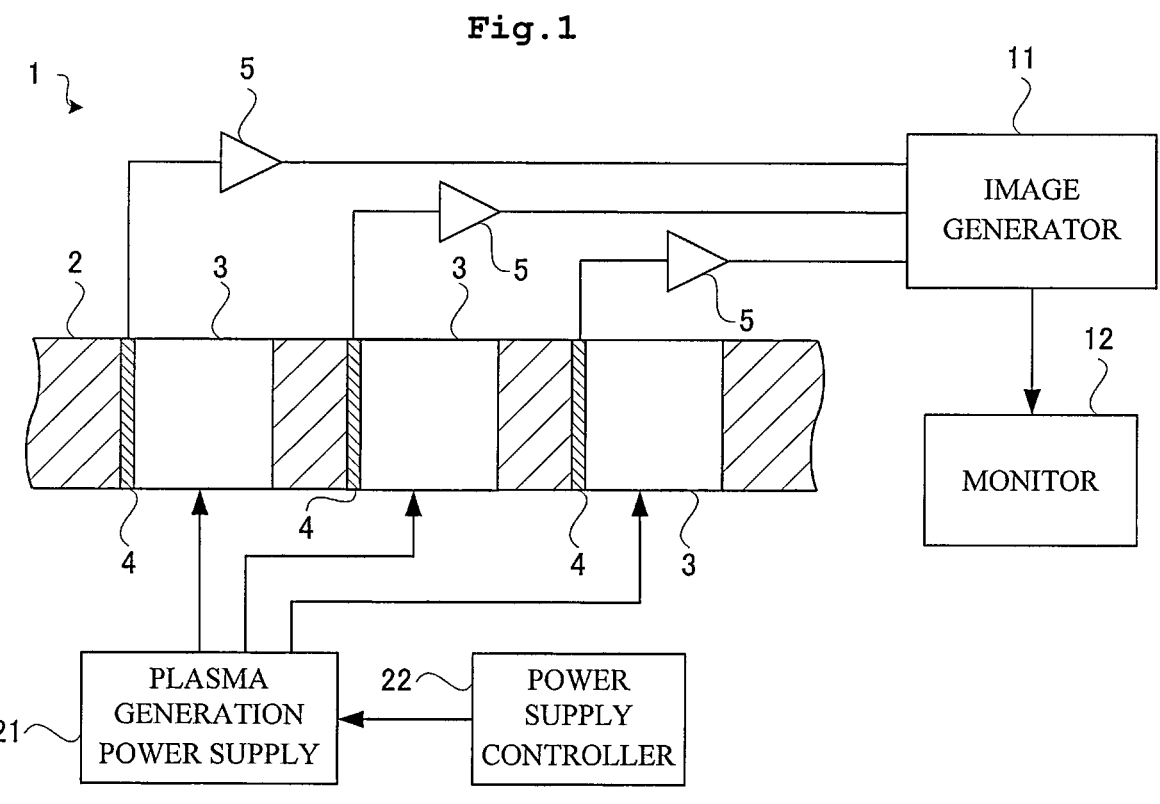
FIG. 1 is a functional block diagram illustrating a configuration of a biomagnetic measuring device according to a first embodiment.

As illustrated in FIG. 1, a biomagnetic measuring device 1 according to the present embodiment includes a support 2 having a plurality of through holes, and a sensor 3 inserted into any of the through holes provided in the support 2. The support 2 is formed of, for example, a helmet covering the head of a subject. The sensor 3 is a magnetic sensor utilizing an optical pumping action. The sensor 3 is configured to output weak magnetism as an optical signal. The optical signal output from the sensor 3 is detected by a photodetector 4 that detects light provided in each of the sensors 3. The photodetector 4 outputs an electric signal indicating the intensity of the detected light. The electric signal is input to a detection circuit 5 provided in each of the photodetectors 4, amplified, and input to an image generator 11. The image generator 11 generates an image such as a magnetoencephalogram based on the input electrical signal. A monitor 12 is configured to display the generated image. The sensor 3 corresponds to a magnetic sensor of the present invention.

Figure 2:
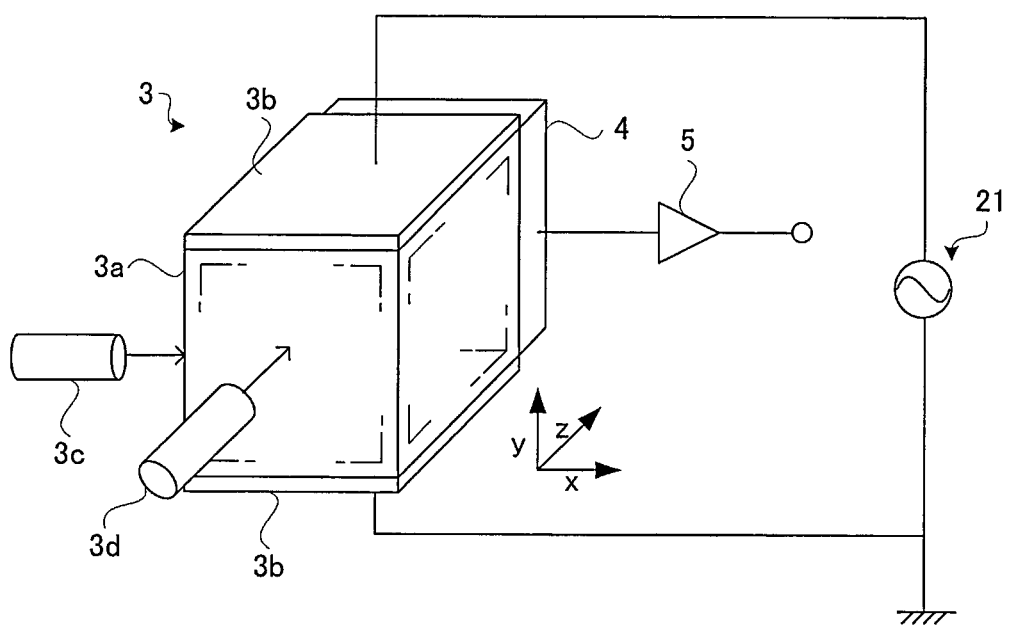
FIG. 2 is a schematic diagram illustrating a configuration of a sensor according to the first embodiment.

The sensor 3 includes a cell 3a (cf. FIG. 2). A plasma generation power supply 21 that generates plasma in the cell 3a of the sensor 3 is connected to the sensor 3. A power supply controller 22 is configured to control the plasma generation power supply 21.

The image generator 11 and the power supply controller 22 are implemented by a central processing unit (CPU) executing various programs. Each unit may be implemented by a single CPU or may be implemented by a plurality of independent processors. A detection circuit controller 13 and a multiplexer controller 14 to be described later may also be implemented by a single CPU or may be implemented by a plurality of independent processors.

FIG. 2 illustrates the configuration of the sensor 3 of the present embodiment and its periphery. As illustrated in FIG. 2, the cell 3a of the sensor 3 has a hexahedral shape with each surface being rectangular (or square). The cell 3a is made of optically transparent quartz, for example, and its inside is hollowed out in accordance with the shape of the cell 3a, so that the cell 3a has a hexahedral internal space. The internal space is filled with a gas suitable for generating plasma, for example, a rare gas (helium gas in the present embodiment). The material of the cell 3a is desirably a dielectric, and may be glass in addition to quartz. It is assumed that two surfaces of the hexahedral shape consti-tuting the cell 3a are orthogonal to the x direction, two surfaces are orthogonal to the y direction, and two surfaces are orthogonal to the z direction. Therefore, the x direction and the y direction are orthogonal, the y direction and the z direction are orthogonal, and the z direction and the x direction are orthogonal.

A plasma generation electrode 3b is provided to cover each of the two surfaces of the cell 3a orthogonal to the y direction. The plasma generation electrode 3b is connected to the plasma generation power supply 21, and an alternat-ing-current (AC) voltage is applied thereto by the plasma generation power supply 21. When an AC voltage is applied to the plasma generation electrode 3b, dielectric barrier discharge occurs in the cell 3a, whereby helium in the cell 3a is converted into plasma.

A pumping light laser 3c is provided at a position where circularly polarized pumping light is emitted from the x direction toward the cell 3a. When the cell 3a is irradiated with the pumping light, the energy level distribution of helium, converted into plasma by the optical pumping action, is biased to a predetermined value.

A probe light laser 3d is configured to emit linearly polarized probe light, distinct from the light of the pumping light laser, from the z direction toward the cell 3a. Plasma-converted helium has optical rotation properties. The angle of optical rotation at this time is a predetermined angle due to the optical pumping action. In this state, when weak magnetism occurs outside the cell, the bias of the energy level of the plasma-converted helium, which has been aligned with a single value, is disturbed, and the angle of optical rotation changes accordingly.

As described above, the sensor 3 is configured to output the input magnetic signal in the form of optical rotation of probe light.

The photodetector 4 is configured to detect probe light having passed through the cell 3a. The photodetector 4 is configured to cause the amount of light detected to change according to the angle of optical rotation. The photodetector 4 converts the amount of probe light detected into an electric signal, and transmits the electric signal to the detection circuit 5. The detection circuit 5 amplifies and outputs the input electric signal.

Figure 3:
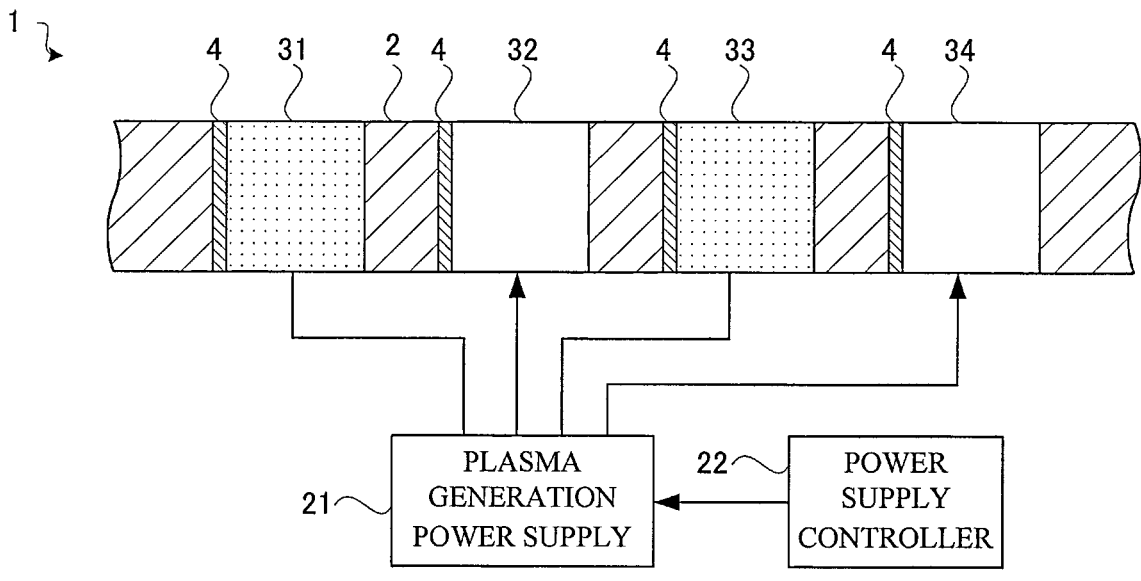
FIG. 3 is an explanatory diagram of the operation of the biomagnetic measuring device according to the first embodiment.

FIG. 3 describes the operation of the power supply controller 22. FIG. 3 depicts four sensors 31, 32, 33, 34, illustrating a state where an AC voltage for generating plasma is not applied to two of the sensors and the AC voltage for generating plasma is applied to the other two sensors. That is, FIG. 3 illustrates a state where the AC voltage is not applied to the leftmost sensor 31 and the AC voltage is applied to the right adjacent sensor 32. Similarly, FIG. 3 illustrates a state where the AC voltage is applied to the rightmost sensor 34 and the AC voltage is not applied to the right adjacent sensor 33. Therefore, FIG. 3 illustrates a state where the sensors 31, 33 to which the AC voltage is not applied and the sensors 32, 34 to which the AC voltage is applied are alternately arrayed.

Figure 4:
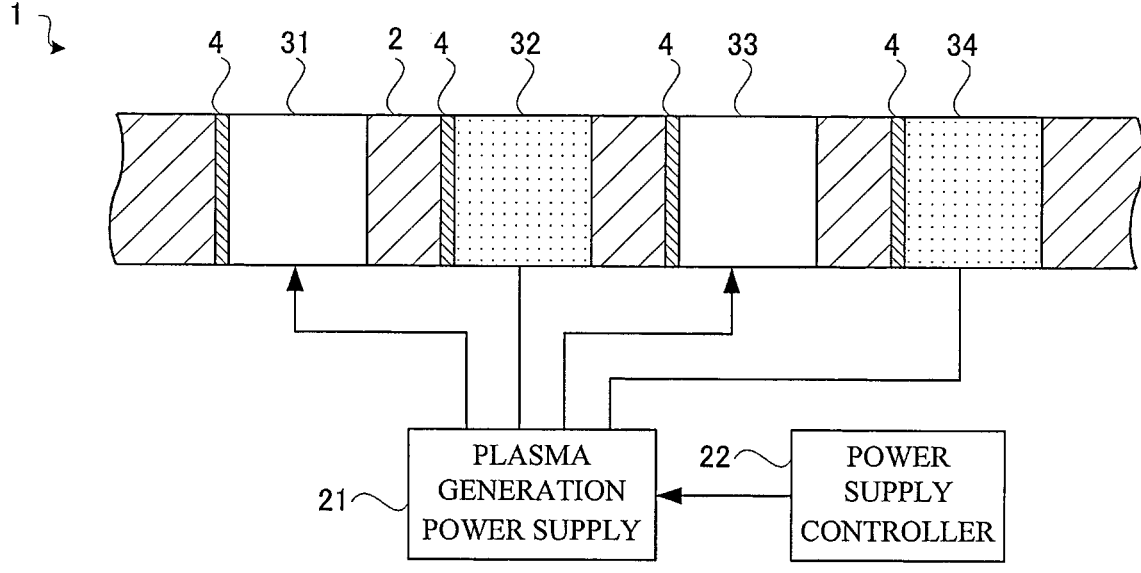
FIG. 4 is an explanatory diagram of the operation of the biomagnetic measuring device according to the first embodiment.

FIG. 4 describes the operation of the power supply controller 22 after a predetermined time has elapsed from FIG. 3. FIG. 4 also depicts four sensors 3, illustrating a state where the AC voltage for generating plasma is applied to two of the sensors and the AC voltage for generating plasma is not applied to the other two sensors. That is, FIG. 4 illustrates a state where the AC voltage is applied to the leftmost sensor 31 and the AC voltage is not applied to the right adjacent sensor 32. Similarly, FIG. 4 illustrates a state where the AC voltage is not applied to the rightmost sensor 34 and the AC voltage is applied to the right adjacent sensor 33. Therefore, FIG. 4 illustrates a state where the sensors 31, 33 to which the AC voltage is applied and the sensors 33, 34 to which the AC voltage is not applied are alternately arrayed.

The power supply controller 22 controls the plasma generation power supply 21 so that the state of FIG. 3 and the state of FIG. 4 are alternately repeated. In the state of FIG. 3, helium plasma is generated in the cells 3a of the second sensor 32 from the left and the rightmost sensor 34, and magnetism can be detected. On the other hand, helium plasma is not generated in the cells 3a of the leftmost sensor 31 and the third sensor 33 from the left, and magnetism cannot be detected. Thus, in the state of FIG. 3, the second sensor 32 from the left and the rightmost sensor 34 detect magnetism.

In contrast, in the state of FIG. 4, helium plasma is generated in the cells 3a of the leftmost sensor 31 and the third sensor 33 from the left, and magnetism can be detected. On the other hand, helium plasma is not generated in the cells 3a of the second sensor 32 from the left and the rightmost sensor 34, and magnetism cannot be detected. Thus, in the state of FIG. 4, the leftmost sensor 31 and the third sensor 33 from the left detect magnetism.

The power supply controller 22 is configured to detect the magnetism of the four sensors 31, 32, 33, 34 by controlling the plasma generation power supply 21 to repeat the state of FIG. 3 and the state of FIG. 4. Therefore, when the sensor 3 detects magnetism, there is no helium plasma generated in the cells of the sensors 3 on both sides. With this configu-ration, it is possible to suppress an adverse effect on the magnetic detection in a first sensor 3 caused by helium plasma generated in a second sensor 3 adjacent to the first sensor 3.

Figure 5:
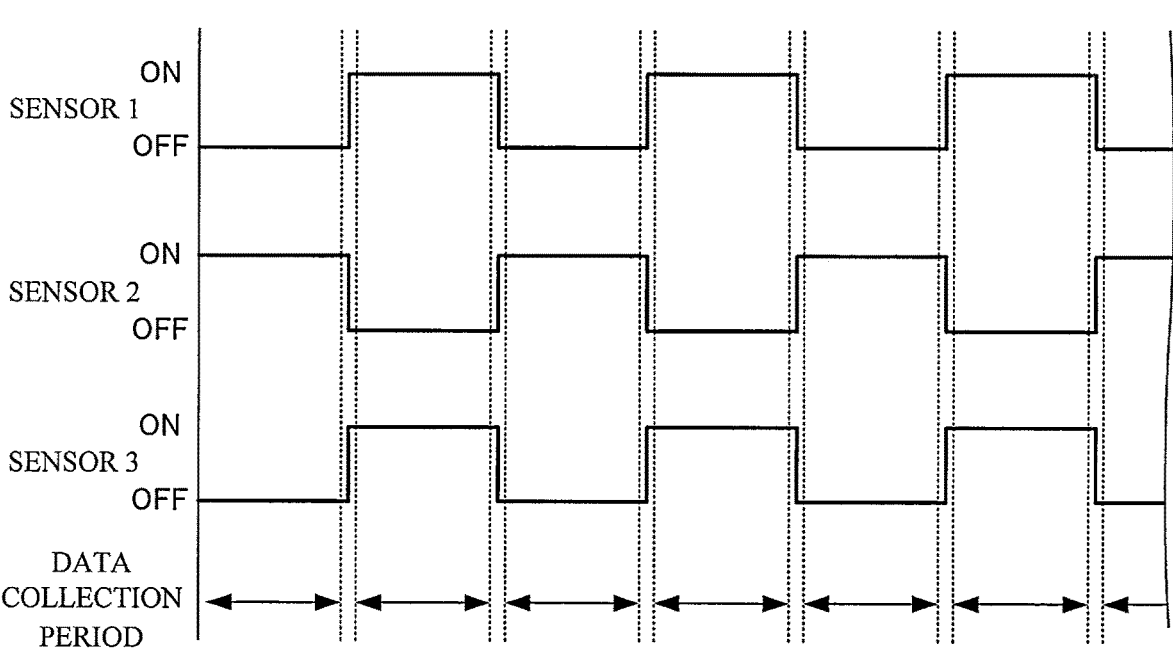
FIG. 5 is a time chart for the operation of the biomagnetic measuring device according to the first embodiment.

FIG. 5 is a time chart illustrating how the power supply controller 22 synchronously turns on the first sensor 3 and turns off the second sensor 3 adjacent to the first sensor 3, and synchronously turns off the first sensor 3 and turns on the second sensor 3. Here, turning on the sensor 3 refers to starting the application of the AC voltage for plasma gen-eration to the sensor 3, and turning off the sensor 3 refers to ending the application of the AC voltage for plasma gen-eration applied to the sensor 3.

That is, the first sensor 3 is turned on at a certain time (first start time) and turned off at a first end time after the first start time. On the other hand, the second sensor 3 is turned on at a second start time later than the first start time pertaining to the first sensor 3, and turned off at a second end time later than the first end time pertaining to the first sensor 3. In the present embodiment, the first end time and the second start time are the same time, but the second start time may be earlier or later than the first end time.

A third sensor 3 is a sensor located relatively away from the first sensor 3 and adjacent to the second sensor 3. The on/off pattern of the sensor included in the third sensor 3 is the same as the on/off pattern of the sensor of the first sensor 3. As described above, in the present embodiment, the control of plasma generation can be matched and common for the two non-adjacent sensors 3. Therefore, according to the present embodiment, while the sensors 3 belonging to the group pertaining to the first sensor 3 are turned on all at once, the sensors 3 belonging to the group pertaining to the second sensor 3 are turned off all at once, and while the sensors 3 belonging to the group pertaining to the second sensor 3 are turned on all at once, the sensors 3 belonging to the group pertaining to the first sensor 3 are turned off all at once. The sensors 3 belonging to the same group are not adjacent to each other.

FIG. 5 also partially illustrates the operation of the image generator 11. The image generator 11 receives an input of an electrical signal based on an optical signal output from the sensor 3 belonging to the group pertaining to the first sensor 3 or the sensor 3 belonging to the group pertaining to the second sensor 3. A first detection circuit 5 connected to the first sensor 3 constantly and continuously transmits an electrical signal to the image generator 11. The image generator 11 is configured to use a part of the transmitted electric signal for image generation. That is, the image generator 11 collects an electrical signal output from the first detection circuit 5 during the period when the first sensor 3 is in the on state and uses the collected electrical signal for image generation. The image generator 11 does not use, for image generation, the electrical signal output from the first detection circuit 5 during the period when the first sensor 3 is in the off state. Such an operation also applies to the other sensors 3 belonging to the group pertaining to the first sensor 3.

Further, such an operation also applies to the second sensor 3. That is, the image generator 11 collects an electric signal output from the second detection circuit 5 connected to the second sensor 3 during the period when the second sensor is in the on state and uses the collected electric signal for image generation. The image generator 11 does not use, for image generation, the electrical signal output from the second detection circuit 5 during the period when the second sensor 3 is in the off state. Such an operation also applies to the other sensors 3 belonging to the group pertaining to the second sensor 3.

More strictly, the collection period of the electric signal used for image generation by the image generator 11 does not include the time point at which the first sensor 3 and the second sensor 3 are turned on and off, as well as immediately before and after this time point. That is, the electric signal collection is started some time after the first sensor 3 is turned on, and the electric signal collection ends before the first sensor 3 is turned off. Similarly, the electric signal collection is started some time after the second sensor 3 is turned on, and the electric signal collection ends before the second sensor 3 is turned off. In this way, the electric signal that is disturbed due to the influence of the on/off of the sensor 3 is not used for image generation, enabling the generation of a magnetoencephalogram with fewer noise components.

In the present embodiment, the first end time and the second start time are the same time, but in a case where the second start time is set earlier than the first end time, there is a period when the first sensor 3 (e.g., the sensor 31) and the second sensor 3 (e.g., the sensor 32) are simultaneously on. The collection period of the electric signal related to the first sensor 3 is executed at least in a period from the first start time to the second start time (a period slightly shorter than the predetermined period described above). In the present embodiment, a magnetic detection signal pertaining to the first sensor 3 may be collected or may not be collected in the period from the second start time to the first end time.

Second Embodiment

Figure 6:
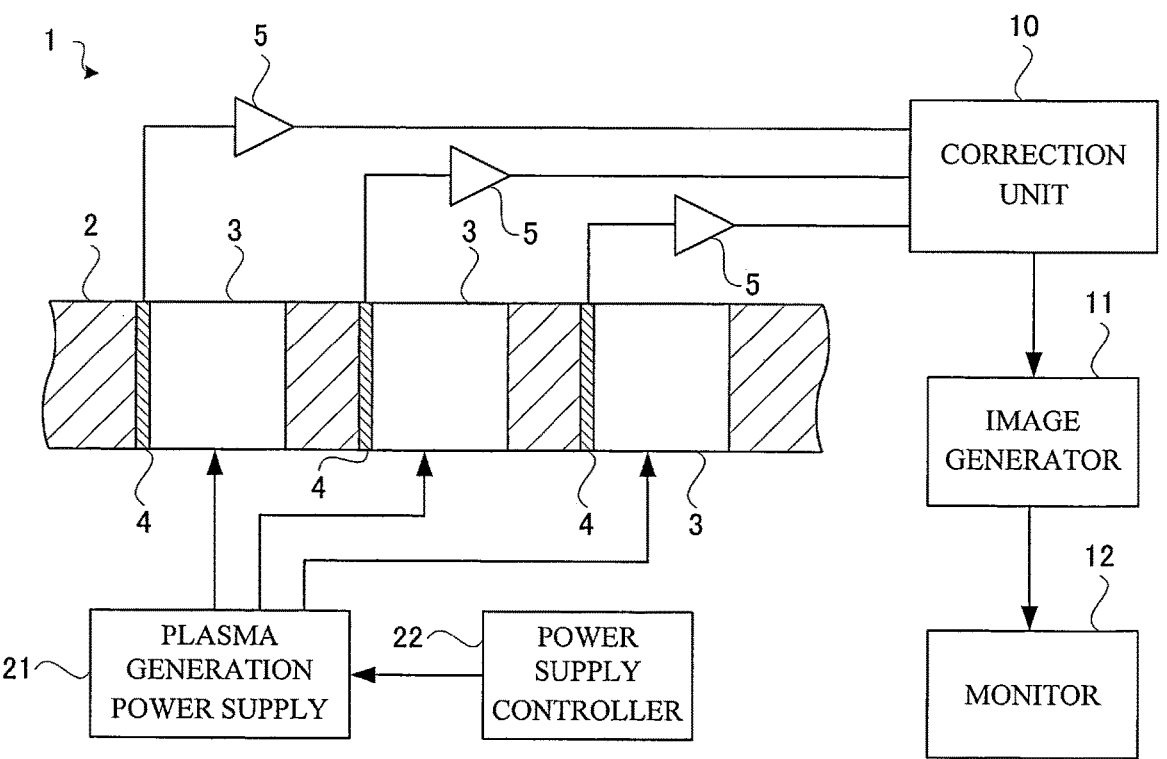
FIG. 6 is a functional block diagram illustrating a configuration of a biomagnetic measuring device according to a second embodiment.

As illustrated in FIG. 6, a device according to a second embodiment includes a correction unit 10 upstream of the image generator 11. In the first embodiment, the electric signal has not been collected when the AC voltage for plasma generation is not applied to the sensor 3. However, in the present embodiment, the electric signal is collected in the period (the period after the first end time) and is used for correcting magnetic detection signal.

The electric signal is constantly and continuously transmitted to the correction unit 10 of the present embodiment from the first detection circuit 5 connected to the first sensor 3. The correction unit 10 collects an electric signal when the first sensor 3 is in the off state as a correction signal. The correction signal includes information on the influence of the aging deterioration of the probe light laser 3d, the fluctuation and the aging deterioration of the photodetector 4, and the material degradation and contamination of the cell 3a. Then, the correction unit 10 collects an electric signal when the first sensor 3 is in the on-state as a magnetic detection signal. More strictly, the collection period of each of the correction signal and the magnetic detection signal by the correction unit 10 does not include the time point at which the first sensor 3 is turned on/off, as well as immediately before and after this time point. This is because the disturbance in the signal due to the on/off of the sensor 3 is superimposed on the electric signal during this period.

In the present embodiment, the first end time and the second start time are the same time, but in a case where the second start time is set earlier than the first end time, there is a period when the first sensor 3 (e.g., the sensor 31) and the second sensor 3 (e.g., the sensor 32) are simultaneously on. The correction unit 10 collects the magnetic detection signal related to the first sensor 3 at least in a period from the first start time to the second start time (a period slightly shorter than the predetermined period described above). In the present embodiment, a magnetic detection signal pertaining to the first sensor 3 may be collected or may not be collected in the period from the second start time to the first end time.

The correction unit 10 calculates a difference between the magnetic detection signal and the correction signal and generates a difference signal. The difference signal is a signal from which components such as the aging deterioration of the probe light laser 3d included in the magnetic detection signal have been removed, and more accurately represents the magnetism of the external field than the magnetic detection signal before correction. The difference signal is transmitted to the image generator 11 and converted into an image such as a magnetoencephalogram.

Third Embodiment

Figure 7:
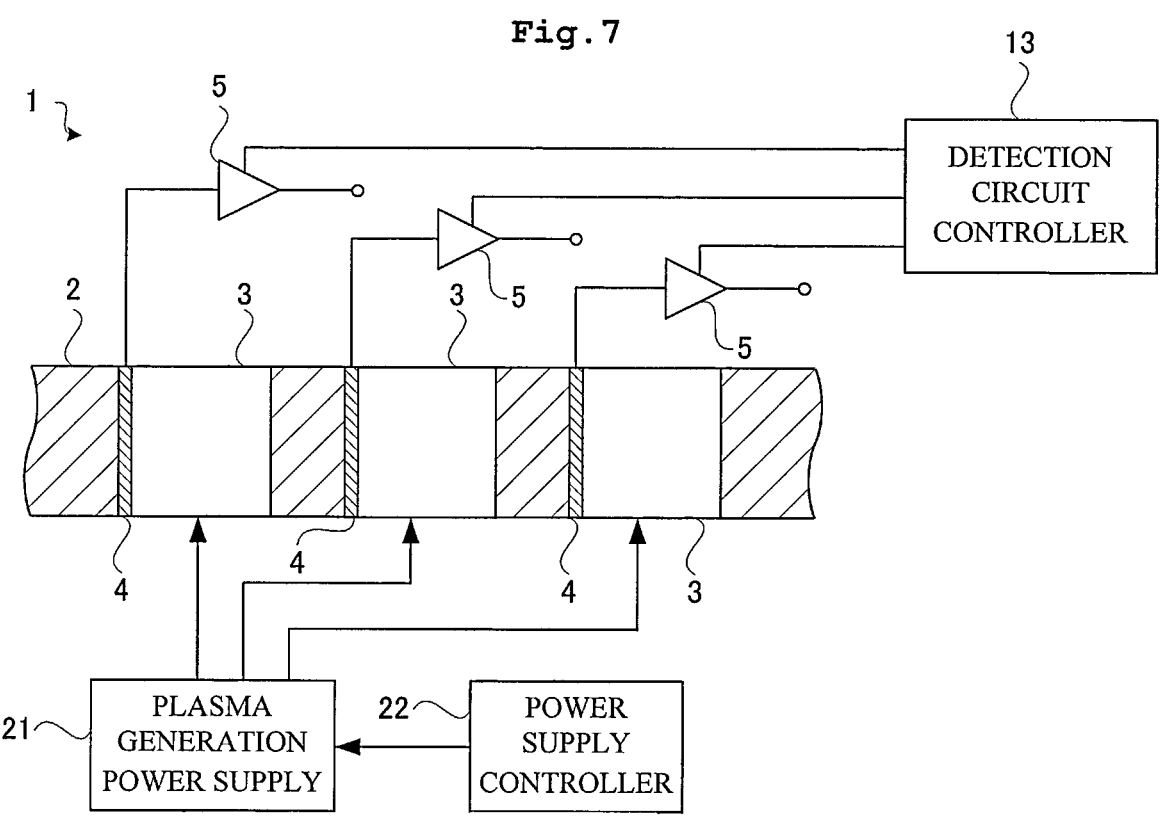
FIG. 7 is a functional block diagram illustrating a configuration of a biomagnetic measuring device according to a third embodiment.

As illustrated in FIG. 7, the device according to a third embodiment includes a detection circuit controller 13 capable of turning on and off the detection circuit 5. The configuration of the third embodiment is characterized in that the detection circuit 5 is turned on and off in accordance with the on and off of the sensor 3. When the detection circuit controller 13 outputs the on signal to the control terminal of the detection circuit 5, the detection circuit 5 is turned on. When the detection circuit controller 13 outputs an off signal to the control terminal of the detection circuit 5, the detection circuit 5 is turned off. When the detection circuit 5 is turned on, the function of converting the optical signal of the sensor 3 corresponding to the detection circuit 5 into the magnetic detection signal is enabled, and when the detection circuit 5 is turned off, the function of converting the optical signal of the sensor 3 corresponding to the detection circuit 5 into the magnetic detection signal is disabled.

Figure 8:
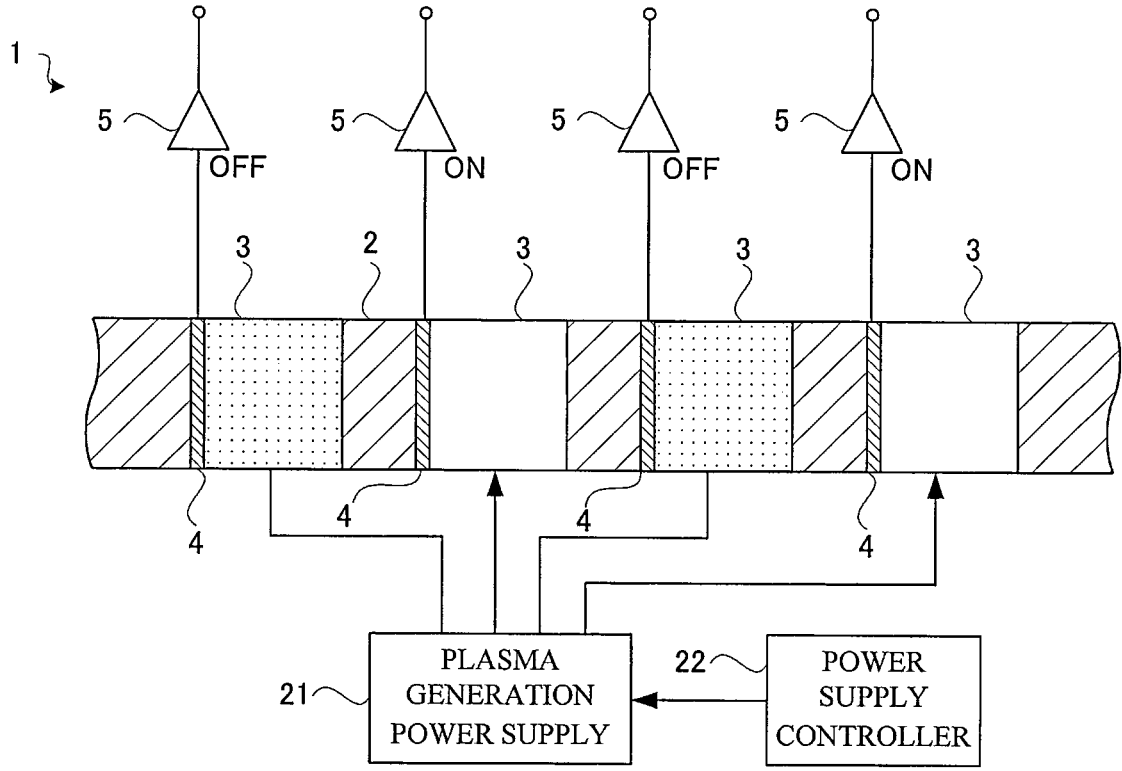
FIG. 8 is an explanatory diagram of the operation of the biomagnetic measuring device according to the third embodiment.

Basically, as illustrated in FIG. 8, the detection circuit controller 13 of the present embodiment turns on the detection circuit 5 connected to the sensor 3 during a period when the sensor 3 is on, and turns off the detection circuit 5 connected to the sensor 3 during a period when the sensor 3 is off. Therefore, the detection circuit controller 13 of the present embodiment operates in synchronization with the power supply controller 22.

More strictly, the operation of the detection circuit controller 13 is configured to turn on the detection circuit 5 connected to the sensor 3 after the power supply controller 22 turns on the sensor 3, and turn off the detection circuit 5 connected to the sensor 3 before the power supply controller 22 turns off the sensor 3. That is, in the present embodiment, the detection circuit controller 13 is configured to turn on the detection circuit 5 after the first start time and turn off the detection circuit before the first end time. For example, as illustrated in a time chart in FIG. 9, the first detection circuit 5 connected to the first sensor 3 is in the off state at the time point when the first sensor 3 and the second sensor 3 are turned on and off, as well as immediately before and after this time point. This configuration also applies to the second detection circuit 5 connected to the second sensor 3. If the detection circuit 5 is turned on at the time point when the first sensor 3 and the second sensor 3 are turned on and off, as well as immediately before and after this time point, the detection circuit 5 will continuously transmit an output signal to the image generator 11 during this time. The output signal at this time is disturbed due to the influence of the on/off of the sensor 3. According to the present embodiment, while the sensor 3 is turned on and off, the detection circuit 5 remains off and the magnetic detection signal is not collected. Therefore, such disturbance in the output signal is not transmitted to the image generator 11.

In the present embodiment, the first end time and the second start time are the same time, but in a case where the second start time is set earlier than the first end time, there is a period when the first sensor 3 (e.g., the sensor 31) and the second sensor 3 (e.g., the sensor 32) are simultaneously on. The detection circuit controller 13 turns on the detection circuit 5 connected to the first sensor 3 at least in a period from the first start time to immediately before the second start time (a period slightly shorter than the predetermined period described above). In a period from the second start time to the first end time, the detection circuit 5 pertaining to the first sensor 3 may remain on, or the detection circuit 5 pertaining to the first sensor 3 that is in the on state before the second start time may be turned off.

Effects of Configuration of Embodiment

Hereinafter, the configuration of the biomagnetic measuring device 1 in the present embodiment and its effects will be described.

(1) A biomagnetic measuring device 1 of the present embodiment includes: a sensor 31 and a sensor 32 that each include a cell 3a having an internal space, and detect biomagnetism utilizing an optical pumping action by plasma generated in the cell 3a: a plasma generation power supply 21 that supplies electric power for generating plasma in the internal space of each of the cells 3a included in the sensor 31 and the sensor 32; and a power supply controller 22 that controls the plasma generation power supply 21 to generate plasma in the sensor 31 from a first start time to a first end time and generate plasma in the sensor 32 from a second start time after the first start time to a second end time after the first end time.

As described above, when the plasma generation power supply 21 is controlled so that the periods during which plasma is generated in the sensor 31 and in the sensor 32 are different from each other, the sensors do not adversely affect magnetic measurement, making it possible to provide a biomagnetic measuring device that can measure biomagnetism more accurately.

(2) In the biomagnetic measuring device 1 according to (1), the sensor 31 detects biomagnetism at least in a predetermined period from the first start time to the second start time.

As described above, when the sensor 31 detects the biomagnetism at least in a predetermined period from the first start time to the second start time, the sensor 32 can detect the biomagnetism without being affected by the cell 3a of the adjacent sensor 31. Therefore, with the configuration described above, it is possible to provide a biomagnetic measuring device that can measure biomagnetism more accurately.

(3) In the biomagnetic measuring device 1 according to (1) or (2), the first end time is the same time as the second start time or a time before the second start time.

As described above, when the first end time is the same time as the second start time or before the second start time, the generation period of the plasma in the sensor 31 and the generation period of the plasma in the sensor 32 are prevented from overlapping with each other, so that the sensor 31 can detect the biomagnetism without being affected by the adjacent sensor 32 in the entire period from the first start time to the first end time.

(4) The biomagnetic measuring device 1 according to any of (1) to (3) further includes a correction unit 10 that corrects a magnetic detection signal of the sensor 31 by taking a difference between a magnetic detection signal detected by the sensor 31 in a predetermined period from the first start time to the second start time and a magnetic detection signal detected by the sensor 31 outside the predetermined period.

By providing the correction unit 10 as described above, it is possible to eliminate the influence of aging deterioration or the like of the cell 3a included in the magnetic detection signal. Therefore, with the configuration described above, it is possible to provide a biomagnetic measuring device that can measure biomagnetism more accurately.

(5) The biomagnetic measuring device 1 according to any of (1) to (4) further includes a sensor 33 located at a position farther from the sensor 31 than the sensor 32. The power supply controller 22 controls the plasma generation power supply 21 to overlap periods during which plasma is generated in the sensor 31 and in the sensor 33.

When the power supply controller 22 that performs control as described above is provided, the control method for the sensor 31 can be applied to the control of another sensor 33, thus providing a biomagnetic measuring device with simplified control in the device.

(6) The biomagnetic measuring device 1 according to any of (1) to (5) further includes: a photodetector 4 and a detection circuit 5 that convert an optical signal of the sensor 31 into an electric signal; and a detection circuit controller 13 that enables or disables the photodetector 4 and the detection circuit 5 for the sensor 31. The detection circuit controller 13 enables the photodetector 4 and the detection circuit 5 in a predetermined period from the first start time to the second start time and disables the photodetector 4 and the detection circuit 5 at least in a period after the first end time.

When the detection circuit controller 13 as described above is provided, the photodetector 4 and the detection circuit 5 are turned off and do not output a signal at least in a period after the first end time, so that it is possible to prevent the generation of output of the photodetector 4 and the detection circuit 5 without a result of magnetism detection. With this configuration, it is possible to provide a biomagnetic measuring device that can reliably detect biomagnetism.

(7) In the biomagnetic measuring device 1 according to (6), the detection circuit controller 13 enables the photodetector 4 and the detection circuit 5 after the first start time, and disables the photodetector 4 and the detection circuit 5 before the first end time.

When the detection circuit controller 13 as described above is provided, the photodetector 4 and the detection circuit 5 are turned off during the operation to start generating plasma in the sensor 31 and the operation to eliminate plasma. With this configuration, the operation is performed without collecting the disturbance in the output of the photodetector 4 and the detection circuit 5 caused by the on/off switching of the sensor 31, making it possible to provide the biomagnetic measuring device that can measure the biomagnetism more accurately.

(8) A control method for a biomagnetic measuring device 1 of the present embodiment includes steps, the biomagnetic measuring device 1 including a sensor 31 and a sensor 32 that each include a cell 3a, in which plasma is generated, and detect biomagnetism utilizing an optical pumping action to output the biomagnetism as an optical signal, a plasma generation power supply 21 that supplies electric power for generating plasma to each of the cells 3a, and a power supply controller 22 that controls the plasma generation power supply 21, the steps being: a first step of generating plasma in the cell 3a included in the sensor 31; and a second step of generating plasma in the cell 3a included in the sensor 32 after a predetermined time has elapsed from the first step.

According to the control method including the first step and the second step as described above, it is possible to provide a control method for a biomagnetic measuring device that can measure biomagnetism more accurately by preventing sensors from adversely affecting each other in magnetic measurement.

(9) The biomagnetic measuring device 1 of the present embodiment includes: a sensor 3 including a pair of plasma generation electrodes 3b and a dielectric (quartz) provided at a position sandwiched between the pair of plasma generation electrodes 3b, the sensor 3 including a cell 3a in which plasma is generated through dielectric barrier discharge: a plasma generation power supply 21 that supplies electric power for generating plasma to the cell 3a; and a power supply controller 22 that controls the plasma generation power supply 21.

As described above, with the configuration in which plasma is generated utilizing the dielectric barrier discharge, it is possible to provide a biomagnetic measuring device that can detects the biomagnetism more reliably.

OTHER EMBODIMENTS

Note that the embodiments disclosed herein are illustrative in all respects and are not restrictive. The scope of the present invention includes the claims and all modifications within the meaning and scope equivalent to the claims. As examples, the present invention can be modified as follows.

Figures 9, 10:
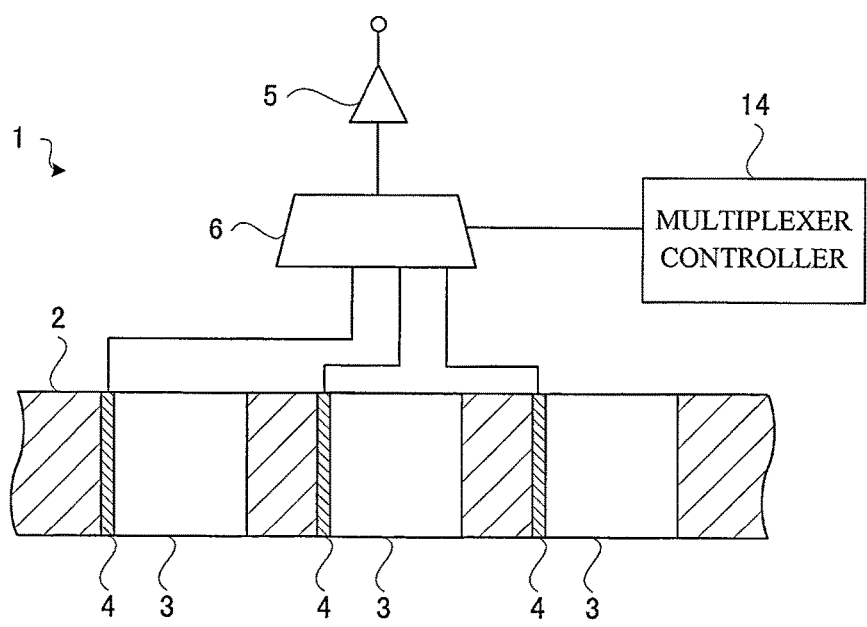
FIG. 9 is a time chart for the operation of the biomagnetic measuring device according to the third embodiment.
FIG. 10 is a functional block diagram illustrating a configuration of a biomagnetic measuring device according to a modification.

(1) In the embodiments described above, one sensor 3 has included one detection circuit 5, but the present invention is not limited to this configuration. As illustrated in FIG. 10, if the multiplexer 6 is provided between the sensor 3 and the detection circuit 5, the detection circuit 5 can be shared by a plurality of sensors 3. In the embodiments described above, except for the configuration according to the second embodiment, half of the detection circuit 5 included in the biomagnetic measuring device 1 does not function. Therefore, the present embodiment includes the multiplexer 6 that sequentially transmits the output of the photodetector 4 connected to each of to the plurality of sensors 3 to the detection circuit 5. The multiplexer 6 inputs the output of the first photodetector 4 to the detection circuit 5 when the first sensor 3 is in the on state. Similarly, the multiplexer 6 inputs the output of the second photodetector 4 to the detection circuit 5 when the second sensor 3 is in the on state. Hereinafter, similarly, each sensor 3 is sequentially turned on, and the output of the photodetector 4 corresponding to the sensor 3 in the on state is input to the detection circuit 5. Such control of the multiplexer 6 can be realized by the multiplexer controller 14. With such a configuration, it is possible to provide a biomagnetic measuring device with a reduced number of components.

(2) In the biomagnetic measuring device of modification (1) described above, the multiplexer 6 has been provided on the detection circuit 5 side, but the multiplexer 6 may be provided on the plasma generation power supply 21 side, and the control regarding the application of the AC voltage may be realized by the multiplexer 6. That is, according to the present embodiment, the AC voltage is alternatively applied to the plurality of sensors 3 through the common multiplexer 6. By alternatively supplying electric power to each of the sensors 3, overlaps in periods during which plasma is generated can be prevented, not only between the adjacent sensors 3 but also among the plurality of sensors 3 controlled by the multiplexer 6.

(3) In the embodiments described above, plasma has been generated through dielectric barrier discharge, but the present invention is not limited to this configuration. Plasma may be generated by other methods such as radio frequency (RF) discharge.

(4) In the embodiments described above, the cell 3a has been configured to be filled with the helium gas, but the present invention is not limited to this configuration, and a configuration using another rare gas or the like is also conceivable. That is, the present invention is not limited to helium gas, and can be applied to a biomagnetic measuring device that includes a magnetic sensor configured to generate plasma and functions as a magnetic sensor when a voltage is applied, and lose the function of the magnetic sensor as the plasma disappears when the application of the voltage is stopped.

(5) In the embodiments described above, the first sensor 3 and the second sensor 3 have been simultaneously controlled. However, the present invention is not limited to this configuration, and the second sensor 3 may be turned on after the first sensor 3 is turned off, and the first sensor 3 may be turned on after the second sensor 3 is turned off. In this manner, a period during which the first sensor is turned on and a period during which the second sensor is turned on may be separated from each other over time, and between those periods, a time may be provided during which both sensors 3 are turned off.

(6) In the embodiments described above, the plurality of sensors 3 have been divided into two groups, and the on/off control method for the sensor 3 has been made different between the groups. However, the plurality of sensors 3 may be divided into three or more groups, and the on/off control method for the sensor 3 may be made different among the groups.

(7) In the embodiments described above, the pumping light and the probe light have been emitted by the two laser light sources, respectively. However, the present invention is not limited to this configuration, and the pumping light laser and the probe light laser may be shared, and one laser light source may be omitted.

REFERENCE SIGNS LIST

3 sensor (magnetic sensor)
21 plasma generation power supply (plasma generator)
22 power supply controller

The invention claimed is:

1. A biomagnetic measuring device comprising:
a first magnetic sensor and a second magnetic sensor that each include a cell having an internal space, and detect biomagnetism utilizing an optical pumping action by plasma generated in the cell;
a plasma generator that supplies electric power for generating plasma in the internal space of each of the cells included in the first magnetic sensor and the second magnetic sensor; and
a power supply controller that controls the plasma generator to generate plasma in the first magnetic sensor from a first start time to a first end time and generate plasma in the second magnetic sensor from a second start time after the first start time to a second end time after the first end time;
a converter that converts an optical signal of the first magnetic sensor into an electric signal; and
a conversion controller that enables or disables the converter for the first magnetic sensor,
wherein the conversion controller enables the converter after the first start time, and disables the converter before the first end time.

2. The biomagnetic measuring device according to claim 1, wherein the first magnetic sensor detects biomagnetism in at least a predetermined period from the first start time to the second start time.

3. The biomagnetic measuring device according to claim 1, wherein the first end time is the same time as the second start time or a time before the second start time.

4. The biomagnetic measuring device according to claim 1, further comprising a correction unit that corrects a magnetic detection signal of the first magnetic sensor by taking a difference between a magnetic detection signal detected by the first magnetic sensor in a predetermined period from the first start time to the second start time and a magnetic detection signal detected by the first magnetic sensor outside the predetermined period, wherein the predetermined period includes the entire period from the first start time to the second start time.

5. The biomagnetic measuring device according to claim 1, further comprising a third magnetic sensor located at a position farther from the first magnetic sensor than the second magnetic sensor,
wherein the power supply controller controls the plasma generator to overlap periods during which plasma is generated in the first magnetic sensor and in the third magnetic sensor.

6. A control method for a biomagnetic measuring device that includes:
a first magnetic sensor and a second magnetic sensor that each include a cell, in which plasma is generated, and detect biomagnetism utilizing an optical pumping action to output the biomagnetism as an optical signal,
a plasma generator that supplies electric power for generating plasma to each of the cells, and
a power supply controller that controls the plasma generator,
a converter that converts the optical signal of the first magnetic sensor into an electric signal; and
a conversion controller that enables or disables the converter for the first magnetic sensor,
the control method comprising:
a first step of generating plasma in the cell included in the first magnetic sensor from a first start time to a first end time; and
a second step of generating plasma in the cell included in the second magnetic sensor after a predetermined time has elapsed from the first step,
wherein the conversion controller enables the converter after the first start time, and disables the converter before the first end time.

* * * * *